United States Patent [19]

Whitney et al.

[11] 4,236,793

[45] Dec. 2, 1980

[54] OPHTHALMIC REFRACTING DEVICE

[75] Inventors: Donald B. Whitney, Southbridge; Bernard Grolman, Worcester; William Richards, Medway, all of Mass.

[73] Assignee: American Optical Corporation, Southbridge, Mass.

[21] Appl. No.: 945,168

[22] Filed: Sep. 25, 1978

Related U.S. Application Data

[63] Continuation-in-part of Ser. No. 891,774, Mar. 30, 1978, abandoned.

[51] Int. Cl.³ .................. A61B 3/04; G02C 7/08; G03B 1/00
[52] U.S. Cl. .................................. 351/21; 351/19; 351/156; 351/58
[58] Field of Search ........... 351/1, 19, 21, 22, 23, 351/20, 158, 47, 57, 128, 48, 58, 156

[56] References Cited

U.S. PATENT DOCUMENTS

| | | | |
|---|---|---|---|
| 1,457,494 | 6/1923 | Bugbee | 351/21 |
| 1,596,019 | 8/1926 | Nelson | 351/156 |
| 1,631,559 | 6/1927 | Stevenson | 351/21 |

OTHER PUBLICATIONS

Frey, Fit Over Trial Frame, Amer. Journ. of Opthal. Issue 10, p. 1501, 1952 (Oct.).

Primary Examiner—John K. Corbin
Assistant Examiner—Rodney B. Bovernick
Attorney, Agent, or Firm—Jeremiah J. Duggan; Alan H. Spencer

[57] ABSTRACT

A fixture for use in refracting an aphakic eye over a properly patient fitted spectacles frame glazed with major spherical component lenses and placed in a position of use upon the patient. The fixture, having trial lens holders for right and left eye refraction, is attached to rims of the spectacles frame for establishing parallelism of the holders with the frame and provision is made for separately adjusting each right and left eye lens holder vertically and horizontally as needed for centering with a corresponding glazed lens. Refraction over the major lens in each case may be conducted with trial lenses placed in the respective holders.

2 Claims, 9 Drawing Figures

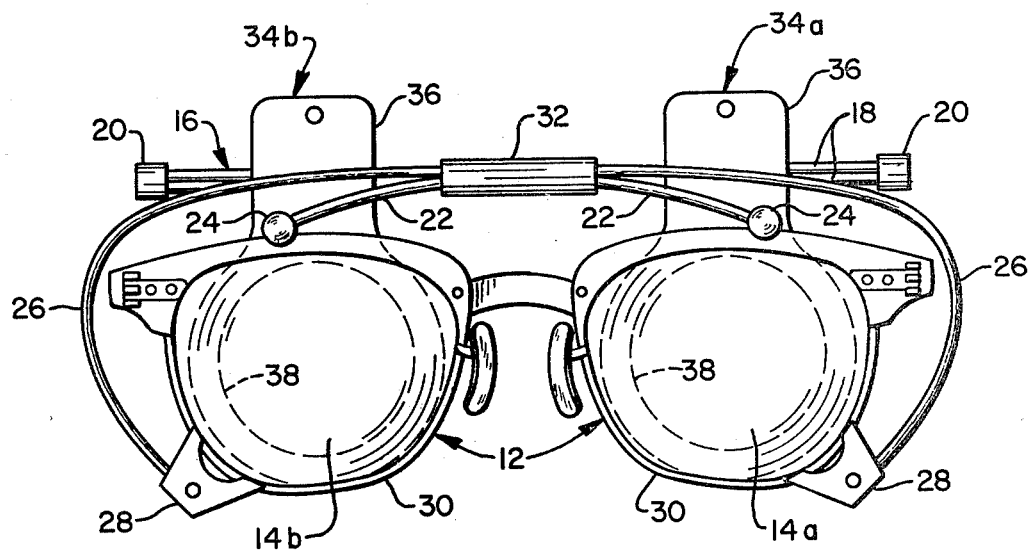
FIG. 4
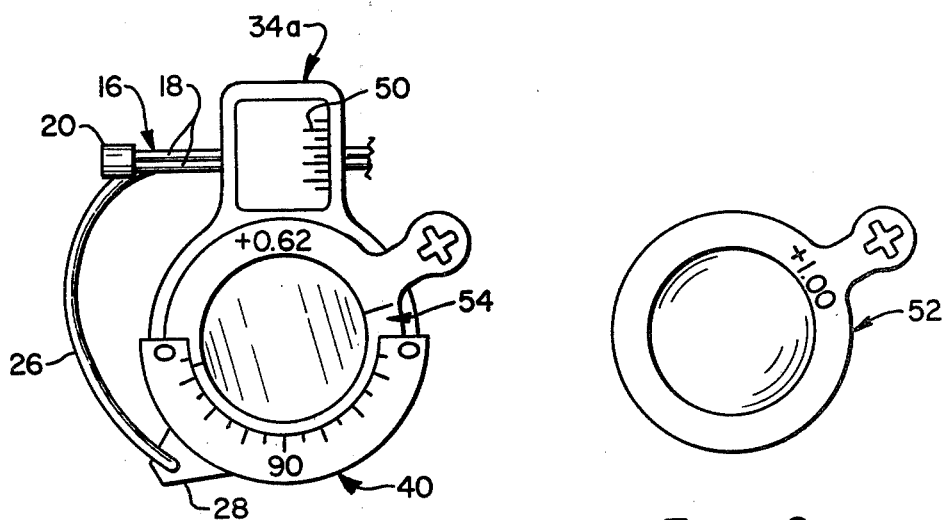
FIG. 5
FIG. 6

OPHTHALMIC REFRACTING DEVICE

BACKGROUND OF THE INVENTION

This is a Contination-in-Part of Application Ser. No. 891,774, filed Mar. 30, 1978, now abandoned.

FIELD OF THE INVENTION

This invention relates to ophthalmic refracting devices and has particular reference to a fixture for "over refracting" aphakics.

DISCUSSION OF THE PRIOR ART

After removal of the crystalline lens and healing, the eye has the potential for acute vision with correction of the resultant refractive error. Success of the procedure as judged by the patient, however, depends primarily on the accuracy with which the refractive error is corrected.

Test procedures for exploiting an aphakic eye's potential are basically no different from those employed in the working with of any refractive error. However, management of the aphakic differs significantly in the implementation of the refraction findings in a fitted spectacles situation.

While unwanted optical errors may go undetected in low to moderate ophthalmic corrections, those of the "cataract" range of approximately 10 times in amplitude exact significant penalties in lens-eye performance. Optimal dispensing requires precise knowledge of the orientation of test lenses which during refraction, yield comfort and maximum acuity. This may be accomplished with a technique well known and referred to as "over refraction".

Over refraction is practiced with a major spherical component (e.g. a 12 diopter lens) glazed in the same or similar frame to be dispensed and fitted carefully as if for permanent wear. By standard refraction test procedure, additional sphere and cylinder corrections are determined by placing sphere and cylinder test lens components before the major component. The efficacy of this procedure is a consequence of duplicating in dispensing the orientation which the major spherical component occupied in refraction.

In the practice of over refraction heretofor, a separate trial lens clip was clamped to each glazed major component for supporting the test lens components, i.e. trial lenses. Each clip required separate vertical and horizontal adjustment without means or benefit of referencing with its counterpart. Accordingly, an assurance of accurate similar alignment of trial lenses before the two glazed major components and parallelism with the spectacles frame is lacking, notwithstanding the drawbacks of general ungainliness in having to handle the clips separately rather than as a unit and store the same in a manner assuring against their separation and/or misplacement of one from another.

In view of parallelism with the spectacles frame and relative alignment of the trial lens holders being critical to the results of over refraction, it is an object of this invention to accomplish this in a uniquely simple, inexpensive and efficient manner.

More particularly, it is another object of the invention to provide an improved "over refraction" fixture which overcomes the problems and drawbacks of prior art trial lens clips.

Still another object is to provide an ophthalmic fixture which has utility in the practice of refracting low to moderate ophthalmic corrections as well as stronger refractive errors of aphakics or other low-vision patients, the fixture further having utility with unglazed, as well as glazed patient fitted spectacles frames.

Other objects and advantages of the invention will become apparent from the following description.

SUMMARY OF THE INVENTION

The foregoing objects and their corollaries are accomplished by the provision of a refracting fixture having a pair of trial lens holders suspended from a normally horizontally disposed main supporting bar. Means for locating and clamping the fixture to a patient's spectacles frame includes grooved locating rollers adjacent the main supporting bar which are adapted to engage tops of the spectacles lens rims and spring loaded aligning blocks adapted to fit against the sides and bottoms of respective lens rims. An elastic strap adapted to extend around the spectacles bridge may be substituted for the aligning blocks. The fixture is firmly clamped in place upon the spectacles frame by the spring loaded blocks or elastic strap and parallelism of the fixture and spectacles frame is established by the locating rollers. The trial lens holders are The trial lens holders are individually adjustable horizontally and vertically on the main supporting bar and are provided with means for establishing and maintaining parallelism thereof in a direction normal to the extension of the main supporting bar. Detents at the connection of each trial lens holder to the supporting bar permit stepped vertical adjustment thereof with lateral sliding adjustment allowed at each increment of vertical adjustment. Indicia are provided for indicating amounts of vertical adjustment of the lens holders relative to the main supporting bar.

Semi-circular lens pockets extending forwardly of each holder afford means for receiving and supporting conventional trial (test) lenses which may be rotated therein, e.g. for establishing cylinder axis orientation of needed cylinder corrections.

Details of the invention will become more readily apparent from the following description when taken in conjunction with the accompanying drawings.

IN THE DRAWINGS

FIG. 4 is a rear elevational view of the refracting device illustrated in a position of use upon a spectacles frame front;

FIG. 5 is a front elevational view of one trial lens holder component of the refracting device with a cylindrical trial lens illustrated in a position of use therein;

FIG. 6 is an elevational view of a spherical trial lens exemplary of the type which may be positioned immediately behind the trial lens of FIG. 5.

DESCRIPTION OF THE PREFERRED EMBODIMENTS

Figure 1:
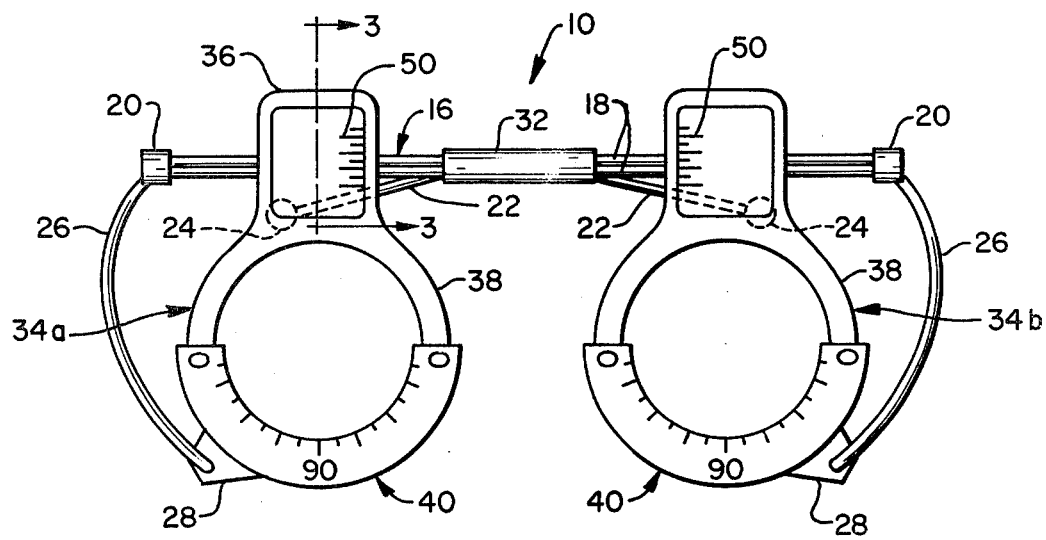
FIG. 1 is a front elevational view of a preferred embodiment of the invention.

Referring more particularly to the drawings, the illustrated embodiment of the invention comprises trial lens supporting fixture 10 adapted to be clamped to a spectacles frame 12 (FIG. 4). While frame 12 need not be glazed, it will be described hereinafter as having the illustrated major spherical component lenses 14a and 14b over which a final correction needed to compensate for a patient's refracting error may be determined with auxiliary trial (test) lenses used in fixture 10.

The structure of fixture 10 includes a normally horizontally disposed main supporting bar 16 which, in the form illustrated, comprises a pair of tightly juxtapositioned wires 18 having end caps 20.

Extending from the central portion of bar 16 in rearwardly spaced relationship therewith are wires 22. These wires are terminated with grooved rollers 24 (FIGS. 2 and 4) which are adapted to fit against the uppermost portions of lens rims or brow portions of the spectacles frame. This establishes parallelism of fixture 10 with frame 12.

Spring tensioned clamping arms 26 extend from adjacent the central portion of bar 16 arcuately laterally and downwardly to grooved blocks 28 which are pivotally attached to the corresponding free ends of the arms. As best shown in FIG. 4, blocks 28 are each rocked into engagement with a portion of the side and bottom of a corresponding spectacles lens rim 30 and held therein-place under the spring tension of arms 26 which, in turn, locks frame 12 in place against locating rollers 24.

The illustrated section of sheathing 32 on bar 16 merely aesthically conceals soldered or brazed connections which may be used to unite wires 18, 22 and arms 26. The sheathing 32 may, however, comprise a metal ferrule crimped or otherwise tightly fastened to bar 16 so as to itself provide and/or reinforce the aforesaid connections.

Supported by bar 16 are right and left trial lens holders 34a and 34b respectively. These holders, being identical, will be described with reference to details of holder 34a only.

Holder 34a comprises an upstanding neck 36 and depending annular portion 38 having a trial lens receiving and supporting pocket 40. Pocket 40 is provided with two semi-circular trial lens compartments 42 and 44, the latter disposed immediately forwardly of the former. While additional compartments may be provided if desired, one compartment 42 suitable for supporting a spherical trial lens component is usually sufficient as will become more readily apparent hereinafter. The spherical and cylindrical trial lenses may be reversed in compartments 42 and 44, if desired. Opposite sides of each of compartments 42 and 44 are provided with recesses 43 and 45 respectively (FIG. 2) for permitting a full 180° rotation of a cylindrical trial lens placed in either.

Figure 2:
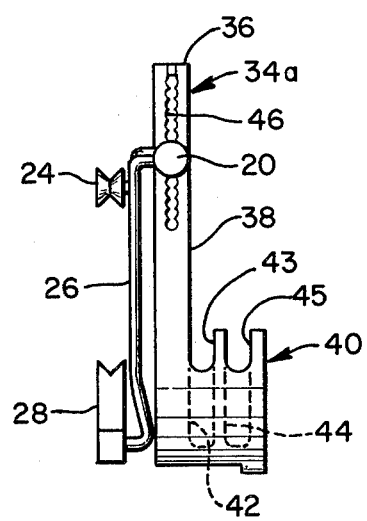
FIG. 2 is a side view of the ophthalmic refracting device of FIG. 1.
Figure 3:
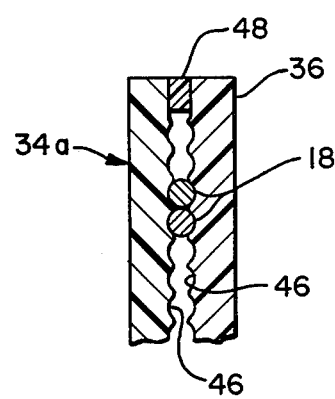
FIG. 3 is a greatly enlarged fragmentary cross-sectional illustration of a portion of a trial lens holder of the refracting device, the cross-section being taken approximately along lines 3—3 of FIG. 1.

Neck 26 of holder 34a is bifurcated as shown in FIGS. 2 and 3 with matching parallel serrations 46 internally of each extension of the bifurcation. These serrations 46 extend horizontally across neck 36 and fit snugly over wires 18 of bar 16 as illustrated in FIG. 3. With holder 34a constructed of a rigid but resilient plastic or other lightweight material including metal, holder 34a may be adjusted upwardly and downwardly on bar 16 by lifting or lowering the same with sufficient force to cause serrations 46 to override wires 18. With each increment of one wire 18 diameter, neck 36 will become fixedly snapped into an adjusted vertical position on bar 16. Its vertical right-angular relationship with bar 16 will, at the same time, be maintained by the parallelism of serrations 46. Holder 34a may be readily horizontally slidably adjusted along bar 16 while at any vertically adjusted position. A frictional force determined by the tightness of serrations 46 against wires 18 prevents accidental horizontal displacement of the holder.

A spacer 48 of a thickness selected in accordance with the width of the bifurcation in neck 36 is provided to establish the proper frictional fit of neck 36 over wires 18.

Indicia 50 (FIG. 1) provide means for indicating relative positions of vertical adjustment of holders 34a and 34b.

Refracting with fixture 12 may be accomplished as follows:

A spectacles frame having a size, shape and style appropriate for a particular low-vision patient, e.g. an aphakic, is selected.

For a patient needing a spherical correction other than 12 diopters as is typical for the aphakic, the frame is glazed with 12 diopter spherical lenses and accurately fitted to the patient. It is so adjusted as to locate optical axes of the 12 diopter spherical components in such positions as to extend as accurately as possible through the center of rotation of the eye in each case of each eye to be refracted.

Fixture 10 is applied to the spectacles frame as illustrated in FIG. 4 and the frame is placed upon the patient in a position corresponding to that intended for permanent dispensing.

Annular portions of holders 34a and 34b are adjusted horizontally and vertically into centered relationship with respective optical axes of lenses 14a and 14b.

With the frame 12 and fixture 10 so positioned and adjusted, refraction procedures are followed to determine the sphere and cylinder (with axis) which in combination with the 12 diopter major component achieves maximum visual acuity. Being an over refraction technique, this is accomplished by placing a spherical trial (test) lens, e.g. lens 52 (FIG. 6), behind a cylindrical trial lens 54 (FIG. 5) in compartments 42 and 44 respectively of pocket 40 in each of holders 34a and 34b. As mentioned heretofore, lenses 52 and 54 may be reversed in pocket 40, if desired.

The powers and cylinder axes of the trial lenses are noted and used in combination with the power of the major spherical component to arrive at the patient's prescription, e.g. for distance viewing correction.

Near-viewing correction may be determined with a plus sphere power trial lens of greater sphere power than the distance trial lens introduced into one of compartments 42 and 44. When a patient's working distance is determined, that aspect of the final prescription may be conventionally computed.

It should be understood that the aforesaid procedure is applicable to either monocular or binocular refraction and that refraction procedures for certain low vision patients may be practiced without the major spherical components 14a and 14b, i.e. with an unglazed spectacles frame 12 and trial lenses only.

Figure 7:
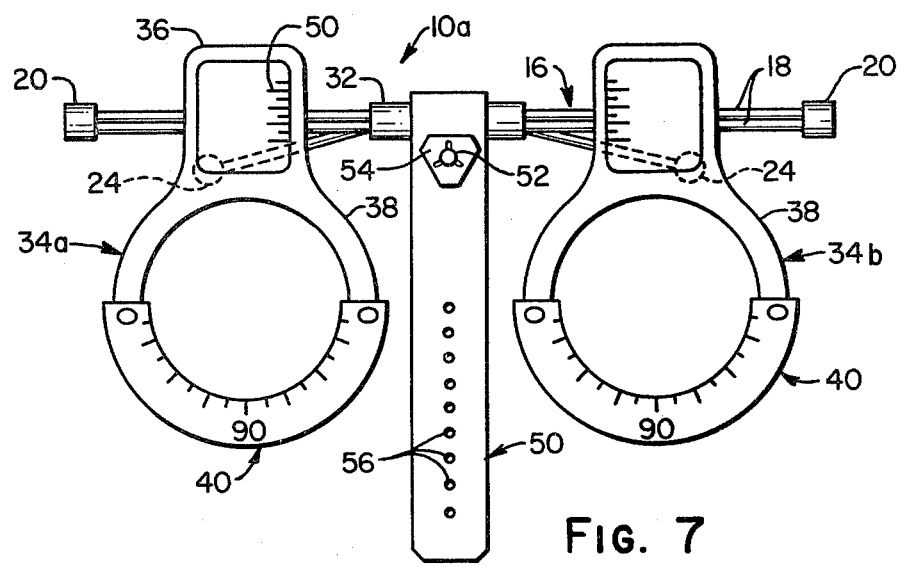
FIG. 7 is a front elevational view of a modification of the invention.
Figure 8:
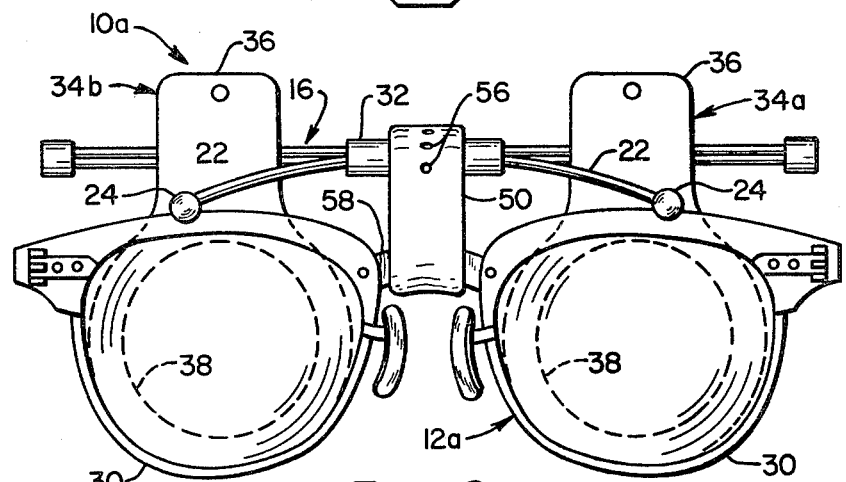
FIG. 8 is a rear elevational view of the refracting device of FIG. 7 illustrated in a position of use upon a spectacles frame front.
Figure 9:
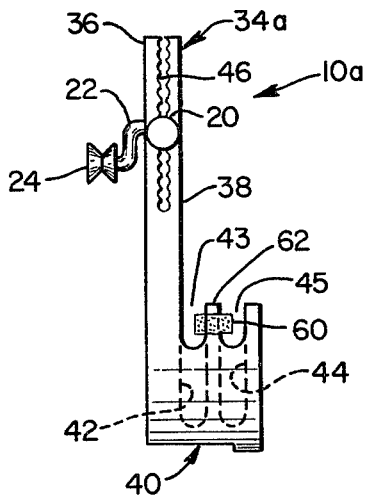
FIG. 9 is a side view of the device of FIGS. 8 and 9.

Referring more particularly to the modification of the invention illustrated by FIGS. 7, 8 and 9, fixture 10a without the clamping arms 26 of fixture 10 is provided with elastic strap 50 for attaching to a spectacles frame 12a (FIG. 8). Strap 50 is fixed to bar 16 over sheathing 32 with collar button-like fastener 52 held in place by spring clip 54. Fastener 52 protrudes forwardly through clip 54 for receiving a selected one of openings 56 in the free end of strap 50. Remaining parts of fixture 10a which correspond to similar parts of fixture 10 are given like reference numerals and need no further description.

In mounting fixture 10a upon frame 12a, grooved rollers 24 are fitted against brow portion of frame 12a to establish parallelism of frame 10a with frame 12a (FIG. 8). Elastic strap 50 is extended beneath bridge 58 and upwardly over its connection to bar 16 whereupon, with tension applied thereto, it is fixed in place by slipping the nearest opening 56 over the forward extension of fastener 52.

With fixture 10a so fitted to frame 12a (as shown in FIG. 8), its use for "over refraction" may be practiced as described hereinabove with reference to fixture 10.

In FIG. 9, there is illustrated a still further modification of the invention which comprises the placement of an annular cushion 60 around the division 62 between recesses 43 and 45 of pocket 40. This cushion, which may be constructed of a flocked fabric, felt, velour, synthetic sponge rubber or other such materials, is provided to prevent undue looseness of trial lenses 52 and 54 in compartments 42 and 44 when placed therein. While cushions 60 permit free rotation of one or both of lenses 52 and 54, accidental displacement from compartments 42 and 44 and/or rattling against the compartment walls is avoided.

Those skilled in the art will readily appreciate that there are various modifications and adaptations of the precise form of the invention here shown and described that may suit particular requirements. Accordingly, the foregoing illustration is not to be interpreted as restrictive of the invention beyond that necessitated by the following claims:

We claim:
1. A refracting fixture comprising the combination of:
a main supporting bar;
a pair of trial lens holders suspended right-angularly from said bar, said holders being individually adjustable along a portion of the length of said bar and in directions across said bar, means for maintaining said right-angular disposition of said holders at all positions of adjustment along and across said bar;

means for manually detachably connecting said bar and trial lens holders to a spectacles frame with said holders disposed forwardly of lens supporting rims of said frame, said connecting means including locaters on said fixture for engaging uppermost brow portions of said spectacles frame to establish parallelism of said fixture and frame when said bar and trial lens holders are connected thereto and clamping arms terminated with V-grooved clamping block for terminally engaging portions of said frame below said brow portions to retain said locaters in place against said brow portions when said connection of said bar and trial lens holders is made, said locaters comprising a pair of rollers carried by wires extending from said main supporting bar and said clamping arms being proximally fixed to said main supporting bar with respective extensions thereof directed arcuately downwardly away from said main supporting bar to said clamping blocks.

2. A refracting fixture comprising the combination of:
a main supporting bar including a pair of tightly juxtapositioned wires;
a pair of trial lens holders suspended right angularly from said bar, said holders being individually adjustable along a portion of the length of said bar and in directions across said bar, means for maintaining said right angular disposition of said holders at all positions of adjustment along and across said bar, said disposition maintaining means including a vertically extending bifurcation in each of said holders, opposite sides of which are provided with matching horizontally directed serrations, said serrations being intimately fitted against said wires of said main supporting bar; and means for manually detachably connecting said bar and trial lens holders to a spectacles frame with said holders disposed forwardly of lens supporting rims of said frame.

* * * * *